United States Patent [19]

Timpl

[11] Patent Number: 4,609,629

[45] Date of Patent: Sep. 2, 1986

[54] PROCESS FOR THE IMMUNOLOGICAL DETERMINATION OF PROTEINS IN BODY FLUID WHICH DISPLAY A NON-PARALLEL INHIBITION CURVE TO A REFERENCE INHIBITOR

[75] Inventor: Rupert Timpl, Gauting, Fed. Rep. of Germany

[73] Assignee: Max-Planck-Gesellschaft Zur Foederung der Wissenschaften E.V., Gottigen, Fed. Rep. of Germany

[21] Appl. No.: 643,815

[22] Filed: Aug. 23, 1984

[30] Foreign Application Priority Data

Sep. 1, 1983 [DE] Fed. Rep. of Germany ....... 3331627

[51] Int. Cl.$^4$ ................. G01N 33/563; G01N 33/577; G01N 33/536
[52] U.S. Cl. ........................................ 436/512; 435/7; 436/536; 436/542; 436/548; 436/815
[58] Field of Search ............... 436/512, 536, 548, 815, 436/542; 435/7

[56] References Cited

U.S. PATENT DOCUMENTS

| | | | |
|---|---|---|---|
| 3,966,898 | 6/1976 | Sjöquist et al. | 436/512 |
| 4,200,436 | 4/1980 | Mochida et al. | 436/512 |
| 4,235,869 | 11/1980 | Schwarzberg | 436/536 |
| 4,253,844 | 3/1981 | Limet et al. | 436/512 |
| 4,312,853 | 1/1982 | Timpl | 436/542 |
| 4,397,960 | 8/1983 | Moussebois et al. | 436/512 |
| 4,504,587 | 3/1985 | Timpl et al. | 436/542 |

FOREIGN PATENT DOCUMENTS 2643207 3/1978 Fed. Rep. of Germany ...... 436/512

OTHER PUBLICATIONS

Biochem. J. (1981) 193, 749–755.
Hoppe-Seyler's Z. Physiol. Chem. Bd. 361, S. 1651–1660, Nov. 1980.

*Primary Examiner*—Christine M. Nucker
*Attorney, Agent, or Firm*—Felfe & Lynch

[57] ABSTRACT

The present invention provides a process for the immunological determination of proteins in body fluids which display a non-parallel inhibition curve to a reference inhibitor, wherein specific monovalent antibody fragments are used as antiserum.

16 Claims, 1 Drawing Figure

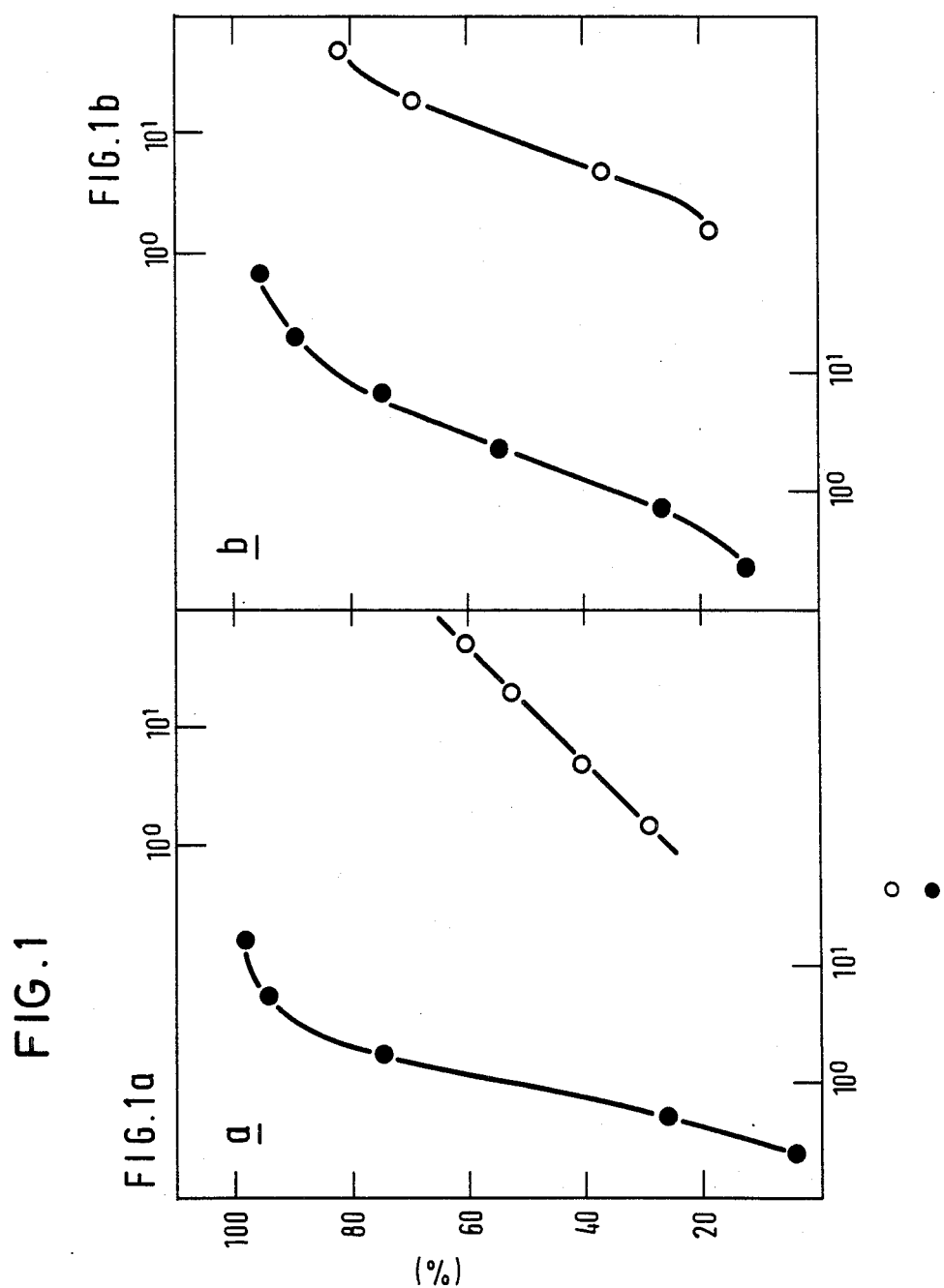

PROCESS FOR THE IMMUNOLOGICAL DETERMINATION OF PROTEINS IN BODY FLUID WHICH DISPLAY A NON-PARALLEL INHIBITION CURVE TO A REFERENCE INHIBITOR

The present invention is concerned with a process for the immunological determination of proteins in body fluids which display a non-parallel inhibition curve to a reference inhibitor.

Immunological processes are standard processes for the specific and quantitative detection of proteins and peptides in body fluids, for example serum or urine, and in tissue extracts, which are characterised by a high sensitivity and specificity and, therefore, have achieved great importance for clinical diagnosis.

The radioimmuno-assay depends upon the fact that an antiserum is prepared in appropriate experimental animals with the help of antigens which are as highly purified as possible, for example proteins or peptides. The antiserum, together with a predetermined amount of radioactively-marked antigen and the body fluid to be investigated, is incubated. If the body fluid contains the corresponding antigen, then less radioactivity is found in the immune complex formed since a part of the radioactively-marked antigen is inhibited by the non-marked antigen present in the body fluid. This inhibition of the radioactively-marked antigen is proportional to the amount of body fluid used. The inhibition reaction is calibrated in a separate batch by the addition of purified antigen of known concentration to the system of marked protein/antiserum. For both inhibitors (purified protein or body fluid), there are usually observed parallel inhibition curves so that the amount of antigen in the body fluid can be calculated from a comparison of both curves.

In the case of the enzyme immuno-assay based upon the same principle, enzymes are used as partners of the immune reaction (EIA, ELISA). Furthermore, there is the possibility of carrying out the marking with fluorochromes.

However, in a series of systems, it has been observed that the inhibition curves of purified reference protein and body fluid display a non-parallel course (see FIG. 1a of the accompanying drawings). The curve of the body fluid is thereby usually less steep than that of the reference protein. This means, of course, a considerable degree of uncertainty in the quantitative evaluation or even makes this impossible. This problem arises especially in the case of extracellular matrix proteins.

A possible explanation of this phenomenon is the assumption that the body fluid does not contain the intact protein but rather a modified form thereof, for example one which is proteolytically broken down and displays a lesser affinity for the antibodies. Other possible explanations comprise a series of technical parameters which have not been characterised in detail, for example high protein concentration or viscosity of the body fluid to be tested which, in a non-specific manner, contribute to a change of the inhibition profile.

A typical observation of this problem was made in the case of the development of a radioimmuno-assay for aminopropeptide (procollagen peptide type III) (Rhode et al., Eur. J. Clin. Invest., 9, 451–459/1979). In this case, the intact peptide could be detected in the serum and, in comparison with authentic aminopropeptide, showed a parallel inhibition curve. Urine, on the other hand, contains a decomposed form of the peptide and its immunological activity is characterised by a non-parallel inhibition curve (see FIG. 1a of the accompanying drawings). A quantitative determination of procollagen in urine is thus not possible.

Therefore, it is an object of the present invention to solve this problem and to provide a process which makes possible a simple quantitative determination of proteins which are present under unfavourable technical conditions.

Thus, according to the present invention, there is provided a process for the immunological determination of proteins in body fluids which display a non-parallel inhibition curve to a reference inhibitor, wherein specific monovalent antibody fragments are used as antiserum.

The use of monovalent antibody fragments in immunological investigations is known from the literature. However, it was previously assumed that normally there is no affinity difference between bivalent antibodies and monovalent antibody fragments. Thus, for example, no difference was found in the inihibiting action of antibodies against creatine kinase on the creatine kinase activity when, for this purpose, use was made of bivalent or monovalent antibodies (U. Würzburg, Kontakte, 3, 10–17/1978).

It was, therefore, surprising to find that the use of monovalent antibody fragments instead of bivalent antibodies leads to a considerable improvement of the inhibition curve in the case of immunological determinations of, for example, extracellular matrix proteins or, in some cases, makes an immunological determination possible for the first time.

Using the example of the aminopropeptide, a comparative analysis of antibodies and monovalent antibody fragments in the immune test with intact procollagen peptide as marked protein and as reference inhibitor showed, in both cases, a comparable detection sensitivity. In the test with the monovalent antibody fragments, urine samples show a parallel inhibition curve and thus permit a dependable quantitative determination of the procollagen peptide type III in this material (see FIG. 1b of the accompanying drawings).

However, the use of monovalent antibody fragments instead of bivalent antibodies is also advantageous in the case of the determination of aminopropeptide in sera. The analysis of the sera shows a five to six times higher concentration of procollagen peptide in the case of measurement with the antibody fragment test in comparison with the measurement of the same sera by means of bivalent antibodies. The biochemical analysis of the sera by means of molecular sieve chromatography shows that about one fifth of the aminopropeptide is present as intact material (molecular weight 45,000) and the remainder as a degraded form (molecular weight 10,000). The test with bivalent antibodies mainly only detects intact aminopropeptide, whereas by means of the antibody fragment test, both forms are included, the sensitivity of the method thereby being improved. The comprehensive analysis of the aminopropeptide in the inactive and in the degraded form with the help of the antibody fragment test represents a valuable extension of serum and urine analyses, for example for the diagnosis of liver fibrosis.

An example of a further protein of the mentioned class, the determination of which in body fluids is of importance for the diagnosis of diabetes and liver diseases, is human laminin P1. Here, too, by means of the use of monovalent antibody fragments, there can be achieved an improvement of the immunological methods of determination. Other examples of proteins for which the present invention can be used include matrix proteins, such as collagens, procollagens and fibronectin.

For the immunological determination of proteins, such as extracellular matrix proteins, with the help of monovalent antibody fragments according to the present invention, there can be used all known immunological methods. For example, all embodiments of the RIA test, for example sequential saturation analyses or equilibrium analyses, marking with chloramine T or Bolton-Hunter reagent (see Felber, Meth. Biochem. Anal., 22, 1/1974; Skelley et al., Clin. Chem. 19, 146–186/1973), can be used. This also applies to the enzyme-immune test. A limitation concerns the separation technique insofar as the test depends upon the Fc portion of the antibody (Fab is missing), for example the complexing of antibodies with protein A from Staphylococci. Other separation processes, for example second antibody in bound or soluble form, are equivalent. Processes with fluorochrome-marked antibodies can also be used.

The antisera can be prepared in the usual way by injecting the antigen into experimental animals, preferably rabbits. It is thereby preferable to work in the presence of complete Freund's adjuvant. There can be administered the amounts of antigen which are usual in such cases, 0.5 to 1 mg. per animal having proved to be an especially suitable dosage in the case of using rabbits. The antiserum formed is then obtained in known manner and can be further purified, for example by means of affinity chromatography methods.

Precipitation with a second antibody against immuno-globulin is an especially appropriate embodiment of the Fab test. The antisera contain sufficient antibodies against Fab for this purpose. Therefore, an immunisation with Fab is not necessary. Especially favourable results have been achieved with goat antisera.

The monovalent antibody fragments can be prepared by the usual processes from the purified antibodies or from the immune globulin fraction of the antisera. In a preferred embodiment, the antibody is borken down by pepsin. Subsequently, it is reduced and, in this way, the Fab' fragment is obtained. In a further preferred embodiment of the invention, Fab fragments are used which are prepared by papain breakdown under reducing conditions.

By means of the present invention, proteins which are otherwise difficult to determine, for example extracellular matrix proteins, can be determined with a high degree of exactitude and very great sensitivity according to immunological methods, whereby the marking can be carried out radioactively or can be replaced by one of the other known markings. For certain proteins for the given class, the present invention makes an immunological determination possible for the first time.

The following Examples are given for the purpose of illustrating the present invention:

EXAMPLE 1

Procollagen III peptide was obtained from foetal calf skin and purified. Antisera were produced in rabbits against procollagen III or procollagen III peptide in the manner described in European Patent Specification No. 0,004,940.

For the RIA test, 25 μg. of the procollagen III peptide were marked with 0.5 1 mCi iodine-125, using the chloramine-T method, and non-bound iodine was removed by dialysis. From the antisera there was obtained the immune globulin G fraction by affinity chromatography on a procollagen III column according to standard processes. These materials were converted by pepsin breakdown and reduction into monovalent Fab' fragments (Nisonoff et al., Arch. Biochem. Biophys., 89, 230–244/1960) or by papein breakdown into monovalent Fab fragments (Mage, Meth. Enzymol., 70, 142–150/1980). The fragments were subsequently separated from non-degraded antibodies or bivalent fragments by molecular sieve chromatography on Sephacryl S-200 (column 1.5×120 cm. in 0.2M ammonium bicarbonate).

The carrying out the RIA test then took place in the presence of a detergent (0.04% Tween 20), such as described in European Patent Specification No. 0,004,940. The precipitation of the immune complex was then carried out with a second antibody against immune globulin G but it can also be carried out by some other known method.

EXAMPLE 2

The procedure described in Example 1 was used but starting from laminin fragment P1 which had been obtained in the manner described in European Patent Specification No. 0,004,940. Marking, purification and the RIA test were carried out in the manner described in Example 1.

EXAMPLE 3

The amounts of aminopropeptides in biological samples were measured according to the process of the present invention with Fab' fragments, using the peptide Col 1–3 as reference inhibitor. The analysis of the serum of 53 normal adults with an age of from 20 to 65 years, as well as 7 urine samples, showed good reproducability, usually with a 10 to 20% variation. The results obtained are set out in the following Table 1.

TABLE 1

| | Reproducability of the values obtained with Fab-RIA for two randomly selected serum and urine samples | | | |
|---|---|---|---|---|
| sample (test A or B)[a] | procollagen peptide amount (ng/ml) measured in the case of dilution[b] | | | average ± S.D. |
| | 1:5 | 1:10 | 1:20 | |
| serum No. 23 A | 26 | 30 | 39 | 32 ± 7 |
| B | 30 | 31 | 28 | 30 ± 2 |
| serum No. 24 A | 30 | 28 | 29 | 29 ± 1 |
| B | 27 | 21 | 29 | 26 ± 4 |
| urine No. 1 A | 59 | 88 | 109 | 85 ± 25 |
| B | 93 | 89 | 99 | 94 ± 5 |
| urine No. 14 A | 47 | 54 | 56 | 52 ± 5 |
| B | 62 | 55 | 52 | 56 ± 5 |

[a]sequential saturation tests carried out on different occasions with two different preparations of marked antigen but the same Fab fragment and reference inhibitor
[b]average of, in each case, 2 determinations per dilution.

I claim:

1. A process for the immunological determination of a protein selected from the group of consisting procollagen III and laminin P1, in a body fluid sample which displays a non-parallel inhibition curve to a reference inhibitor, comprising the steps of
reacting the body fluid sample with labeled specific monovalent antibody fragments,
measuring the extent of the reaction, and comparing the results with results obtained by measuring the reaction of the antibody fragments with the reference inhibitor.

2. A process for the immunological determination of extracellular matrix proteins selected from the group consisting of procollagen III and laminin Pl, in a body fluid sample, comprising the steps of reacting the body fluid sample with a labeled antiserum of specific monovalent antibody fragments, measuring the extent of the reaction and comparing the results with results obtained by measuring the reaction of the antiserum with the reference inhibitor.

3. The process of claim 1 wherein said label is radioactive, and a radioimmunological determination is used to measure the sample and the reference inhibitor reactions.

4. The process of claim 1 wherein the monovalent antibody fragments have been prepared by pepsin breakdown of immune globulin obtained from antiserum raised against the proteins, and subsequent reduction.

5. The process of claim 1 wherein the monovalent antibody fragments have been prepared by papain breakdown of immune globulin from antiserum raised against the proteins, under reducing conditions.

6. The process of claim 1 wherein the protein is procollagen III peptide.

7. The process of claim 1 wherein the protein is laminin P1.

8. The process of claim 1 wherein the protein is antigen fragments and the body fluid is urine.

9. The process of claim 1 wherein the protein is antigen fragments and the body fluid is serum.

10. The process according to claim 2 wherein said label is radioactive, and a radioimmunological determination is used to measure the sample and the reference inhibitor reactions.

11. The process of claim 2 wherein the monovalent antibody fragments have been prepared by pepsin breakdown of immune globulin obtained from antiserum raised against the proteins, and subsequent reduction.

12. The process of claim 2 wherein the monovalent antibody fragments have been prepared by papain breakdown of immune globulin from antiserum raised against the proteins, under reducing conditions.

13. The process of claim 2 wherein the protein is procollagen III peptide.

14. The process of claim 2 wherein the protein is laminin P1.

15. The process of claim 2 wherein the protein is antigen fragments and the body fluid is urine.

16. The process of claim 2 wherein the protein is antigen fragments and the body fluid is serum.

* * * * *